United States Patent
Longo et al.

(10) Patent No.: US 8,425,509 B2
(45) Date of Patent: Apr. 23, 2013

(54) SURGICAL INSTRUMENT FOR PERFORMING CONTROLLED MYOTOMIES

(75) Inventors: Antonio Longo, Palermo (IT); Michele D'Arcangelo, Rome (IT); Alessandro Pastorelli, Rome (IT); Federico Bilotti, Latina (IT); Brian James Thompson, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 779 days.

(21) Appl. No.: 12/438,748

(22) PCT Filed: Jun. 22, 2007

(86) PCT No.: PCT/EP2007/056263
§ 371 (c)(1),
(2), (4) Date: Jan. 6, 2010

(87) PCT Pub. No.: WO2008/028701
PCT Pub. Date: Mar. 13, 2008

(65) Prior Publication Data
US 2010/0106151 A1   Apr. 29, 2010

(30) Foreign Application Priority Data
Sep. 8, 2006   (EP) .................................... 06018865

(51) Int. Cl.
*A61B 18/12*   (2006.01)
(52) U.S. Cl.
USPC .......................................................... 606/45
(58) Field of Classification Search ............... 606/34, 606/41, 45
See application file for complete search history.

(56) References Cited

U.S. PATENT DOCUMENTS

| 5,024,617 | A | * | 6/1991 | Karpiel ........................... 606/47 |
| 5,035,695 | A | | 7/1991 | Weber, Jr. et al. |
| 5,152,772 | A | | 10/1992 | Sewell, Jr. |
| 5,312,407 | A | | 5/1994 | Carter |
| 5,318,565 | A | | 6/1994 | Kuriloff |
| 5,413,575 | A | | 5/1995 | Haenggi |
| 5,423,842 | A | | 6/1995 | Michelson |

(Continued)

FOREIGN PATENT DOCUMENTS

| JP | 10201764 A | 8/1998 |
| JP | 2002542891 A | 12/2002 |

(Continued)

OTHER PUBLICATIONS

EPO Search Report dated Oct. 19, 2007 for corresponding patent application, European Patent Application No. PCT/EP2007/056263 (END5586WOPCT).

*Primary Examiner* — Michael Peffley
*Assistant Examiner* — Daniel Fowler (57) ABSTRACT

A surgical instrument (1) for performing controlled myotomies, particularly for performing internal anal sphincterotomies, comprises a proximal handle portion (2), an elongate insertion shaft (3) connected with the handle portion (2) and extending distally therefrom, a distal incision tip (4) arranged at a distal end of the insertion shaft (3) and adapted to incise tissue distally to the insertion shaft (3), a lateral incision member (5) arranged at the insertion shaft (3) and adapted to incise tissue laterally to the insertion shaft (3), wherein the lateral incision member (4) is movable from a rest position, in which it is retracted towards or inside the insertion shaft (3) and an operational position in which it protrudes laterally from the insertion shaft (3).

13 Claims, 6 Drawing Sheets

U.S. PATENT DOCUMENTS

| | | | |
|---|---|---|---|
| 5,672,173 A * | 9/1997 | Gough et al. | 606/41 |
| 5,810,804 A * | 9/1998 | Gough et al. | 606/41 |
| 6,051,008 A | 4/2000 | Saadat et al. | |
| 6,258,087 B1 * | 7/2001 | Edwards et al. | 606/41 |
| 6,312,429 B1 * | 11/2001 | Burbank et al. | 606/47 |
| 2002/0049423 A1 * | 4/2002 | Howell et al. | 604/528 |
| 2002/0151888 A1 | 10/2002 | Edwards et al. | |
| 2005/0159743 A1 | 7/2005 | Edwards et al. | |
| 2005/0228371 A1 | 10/2005 | West et al. | |
| 2005/0240174 A1 * | 10/2005 | Pearson et al. | 606/41 |
| 2007/0203486 A1 * | 8/2007 | Young | 606/41 |

FOREIGN PATENT DOCUMENTS

| | | |
|---|---|---|
| JP | 2003511193 A | 3/2003 |
| JP | 2004502488 A | 1/2004 |
| JP | 2004505663 A | 2/2004 |
| WO | WO 96/35381 | 11/1996 |
| WO | WO 01/05318 | 1/2001 |
| WO | WO 2006/009705 A2 | 1/2006 |

* cited by examiner

SURGICAL INSTRUMENT FOR PERFORMING CONTROLLED MYOTOMIES

The present invention relates in general to surgical incision or dissecting instruments and particularly to a surgical instrument for performing controlled myotomies such as for instance internal anal sphincterotomies in patients suffering from anal fissure.

Anal fissure is one of the most common disorders of the rectum consisting in a cut or ulcer that usually occurs in either the front or the back of the anus e.g. as a result of a transient bout of constipation or diarrhea. Symptoms of anal fissure usually consist of painful defecation, post-defecatory pain and sparse bleeding. The usual regimen of treatment is to place the patient on medical therapy, stool softeners and lubricate the anal canal with suppositories. While the medical therapy will heal most acute and some less chronic fissures, most of the more chronic fissures will require surgery. The current surgical treatment of choice for chronic anal fissure is internal anal sphincterotomy, and particularly lateral sphincterotomy involving the incision of the internal anal sphincter, thereby releasing tension and allowing the fissure to heal.

The sphincterotomy can be performed in either an open or a closed manner. In a closed sphincterotomy, a scalpel blade is inserted sideways into the intersphincteric groove on a lateral side of the anus. It is then rotated medially and drawn out to cut the internal sphincter. Since the sphincterotomy needs to be extended into the anal canal for a distance equal to the length of the anal fissure, the depth of insertion of the scalpel blade is controlled by palpation of the internal sphincter through the anal mucosa. Moreover, particular care must be taken to not cut the anal mucosa during the medial rotation and proximal withdrawal of the scalpel, because trauma of the mucosa could result in a fistula. In an open sphincterotomy, a 0.5 cm to 1 cm incision is made in the intersphincteric plane. The internal sphincter is then looped on a right angle, brought up into the incision and dissected under direct visualization. The two ends are allowed to fall back after being cut. The extension of the resulting gap in the internal sphincter can be palpated through the anal mucosa, as in the closed technique. The incision is closed by suturing or left open to heal.

Even though the known techniques and surgical instruments for performing the sphincterotomy are satisfactory in releasing the tension on the anus, thereby allowing the anal fissures to heal in about 90-95% of the patients, they are still somewhat invasive. The rotation of the scalpel between the internal and external sphincter can lead to uncontrolled tissue trauma and the manual palpation of the internal sphincter through the anal mucosa does not provide a reliable control of the longitudinal extension of the sphincterotomy. Moreover, the control of the radial (lateral-medial) extension of the incision during operation, which is crucial for avoiding cuts in the anal mucosa, is left to the skill and experience of the surgeon. With regard to the open surgery approach, during operation the internal sphincter is deformed and displaced with respect to the anal fissure which further complicates the control of the myotomy. A less invasive and better controllable operation could further reduce post-operative complications, such as fistula and anal incontinence.

Therefore, the object of the invention is to provide a surgical instrument for the controlled performance of myotomies, particularly for the performance of internal anal sphincterotomies, which consents a less invasive operation and a better control of the position and extension of the myotomy.

This object is achieved by a surgical instrument according to the annexed claim 1. Advantageous embodiments of the invention are the object of the dependent claims.

According to the invention, a surgical instrument for performing controlled myotomies comprises a proximal handle portion, an elongate insertion shaft connected with the handle portion and extending distally therefrom, a distal incision tip arranged at a distal end of the insertion portion and adapted to incise tissue distally to the insertion shaft, a lateral incision member arranged at the insertion shaft and adapted to incise tissue laterally to the insertion shaft, wherein the lateral incision member is movable from a rest position, in which it is retracted towards or inside the insertion shaft and an operational position in which it protrudes laterally from the insertion shaft. This enables the surgeon to insert the instrument by a cutting action of the distal incision tip, whilst the lateral incision member is in the rest position, subsequent extracting of the lateral incision member in its operative position and lateral cutting of tissue by the lateral incision member during the proximal withdrawal of the instrument, without any need to rotate the instrument in the patient's body in order to perform the lateral cut.

In accordance with a further aspect of the invention, the insertion shaft comprises visible and/or tactile markings, preferably a graduated scale which enables the surgeon to visually control the distal insertion depth of the insertion shaft and particularly the insertion depth of the distal incision tip and the lateral incision member. This makes it possible to provide continuous visual control of the cutting depth during the myotomy and obviates manual palpation.

In order to further improve the precision of the myotomy, the operational (laterally protracted) position of the lateral incision member is adjustable in such a way that the surgeon can control and adjust the lateral depth of tissue dissection during the performance of the myotomy. Advantageously, the surgical instrument includes an adjustment cursor or knob which is operatively connected with the lateral incision member and which can be manually brought in a number of different positions (corresponding to a number of differently wide protracted operational positions of the lateral incision member). In order to provide a better control of the lateral incision depth, visible or tactile markings defining a graduated scale are advantageously provided along the track of the adjustment cursor or knob.

The insertion shaft is substantially rigid and straight or curved if required by the anatomic situation and has an elongate flat, approximately plate-like and preferably distally tapered shape defining a reference plane, wherein the lateral incision member can be advantageously extracted transversely (preferably perpendicularly) to the reference plane of the insertion shaft. This particular geometrical configuration allows a stable positioning and a guided withdrawal or advancement of the insertion shaft during a lateral cutting action by the lateral incision member. In this embodiment, the above mentioned visible markings are preferably formed or applied on the external surface of one or both of the two opposite large sides of the insertion shaft.

Even though the distal incision tip and the lateral incision member might be embodied as sharp edged or sharp pointed knife portions in order to cut the tissue, according to the preferred embodiment of the invention both the distal incision tip and the lateral incision member comprise an electrode tip suitable to transmit radiofrequency current to the tissue for dissecting the tissue and coagulating blood. Both, monopolar or bipolar radiofrequency tips can be advantageously utilized.

In accordance with a preferred embodiment, the distal incision tip comprises a blunt radiofrequency current electrode and the lateral incision tip comprises a hook-shaped radiofrequency current electrode wire pointing preferably in a lateral and proximal direction when in the operational position.

In order to reduce the penetration depth of the instrument in the body of the patient, the lateral incision member is advantageously positioned near the distal end of the insertion shaft.

These and other details and advantages of the present invention shall be made apparent from the accompanying drawings and the description thereof, which illustrate embodiments of the invention and, together with the general description of the invention given above, and the detailed description of the invention given below, serve to explain the principles of the present invention.

Figure 1:
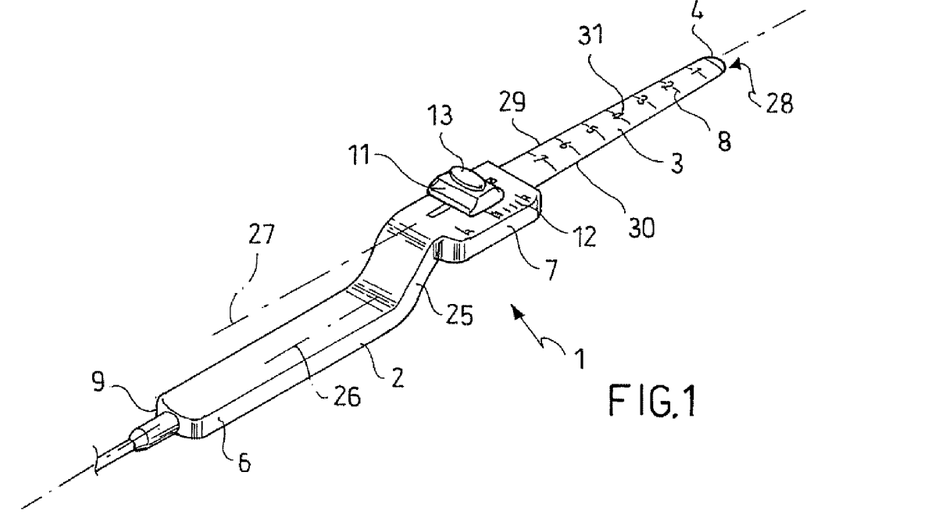
FIG. 1 is a proximal isometric view of a surgical instrument according to a first embodiment of the invention.
Figure 2:
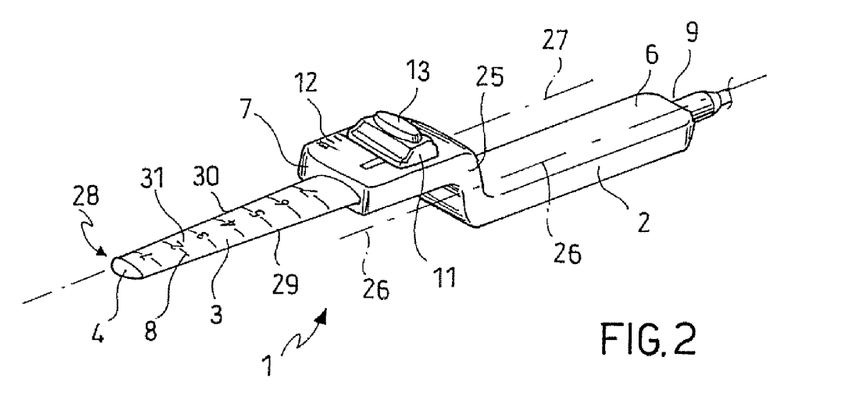
FIG. 2 is a distal isometric view of the surgical instrument of FIG. 1.

Turning to the figures, FIGS. 1 and 2 depict a surgical instrument according to a first embodiment of the invention. The surgical instrument 1 is suitable for performing controlled myotomies such as for instance internal anal shincterotomies to cure chronic anal fissures.

In the following description, the terms "distal" and "proximal" refer to the surgeons viewpoint, if not otherwise indicated.

The instrument 1 comprises a generally elongate body with a proximal handle portion 2 and an elongate insertion shaft 3 extending distally from the handle portion 2. A distal incision tip 4 is arranged at a distal end of the insertion shaft 3 and adapted to incise tissue distally adjacent to the insertion shaft 3. Moreover, a lateral incision member 5 is arranged at near the distal end 28 of the insertion shaft 3 and adapted to incise tissue laterally adjacent to the insertion shaft 3. The lateral incision member 5 is movable from a rest position, in which it is retracted towards or inside the insertion shaft 3 and an operational position in which it protrudes laterally from the insertion shaft 3.

The handle portion 2 has a flat elongate shape, which is approximately rectangular in cross-section, and comprises a distal grip portion 6 and a proximal operating portion 7 provided with a number of controls which will be described later. The operating portion 7, together with the insertion shaft 3 connected thereto, are transversally offset with respect to the grip portion 6 in a direction normal to a plane defined by the flattened grip portion 6, thereby defining a step 25 between the grip portion 6 and the operating portion 7. Due to the resulting transverse offset between the longitudinal axis 26 of the grip portion 6 and the longitudinal axis 27 the operating portion 7 and the insertion shaft 3, the instrument 1 adapts well to the hand of the surgeon and is particularly ergonomic, e.g. for the performance of an anal sphicterotomy.

The insertion shaft 3 is connected and axially aligned with the operating portion 7 of the handle 2 and comprises a substantially straight elongate body which is flattened in the same sense as the handle portion 2 and gradually tapered both towards its distal end 28 and towards two opposite small sides 29, 30. In the embodiment, the insertion shaft 3 has a substantially elliptical cross-sectional shape.

On the external surface of two opposite large sides 31, 32 of the insertion shaft 3 are provided markings 8 which define a graduated visible and/or tactile scale.

The markings 8 make it possible to control the penetration depth of the insertion shaft 3 during operation. In the illustrated embodiment, a centimeter scale from 1 cm to 7 cm is depicted; the scale could have, of course, a different resolution or different length units, such as inches.

At the distal end 28 of the insertion shaft 3 a smoothly rounded blunt radiofrequency (RF) electrode member is arranged which forms the above mentioned distal incision tip 4. The electrode member can be embodied as a single monopolar RF current electrode or, alternatively, as a pair of bipolar RF current electrodes. In case of a monopolar RF system, a single monopolar electrode tip advances a spark between the electrode tip and the tissue. The electrical current generated is attracted to a grounding pad attached to the patient's body. In bipolar RF systems, two closely juxtaposed electrode tips are used to deliver the current to the adjacent tissue.

The distal incision tip 4 is connected to an RF current conductor (not shown in the figures) which is housed inside the insertion shaft 3 and handle portion 2. The RF current conductor extends from the incision tip 4 to an RF connector 9 arranged at the proximal end of the handle portion 2. The RF connector 9 includes preferably a plug-in socket which allows to connect the instrument to an external RF generator. Alternatively, the RF connector 9 is adapted to receive the RF emitting tip of a commercially available surgical RF pen which, in turn, is equipped with an own RF current generator.

The lateral incision member 5 is movable from a rest position, in which it is retracted towards or inside the insertion shaft 3 and an operational position in which it protrudes laterally from the insertion shaft 3. In the embodiment, the lateral incision member 5 includes a monopolar or bipolar radiofrequency electrode member connected to an RF current conductor (not shown in the figures) which is housed inside the insertion shaft 3 and handle portion 2 and extends from the lateral incision member 5 to the above described RF connector 9 in order to connect the lateral incision member 5 to an external RF current generator.

Figure 10:
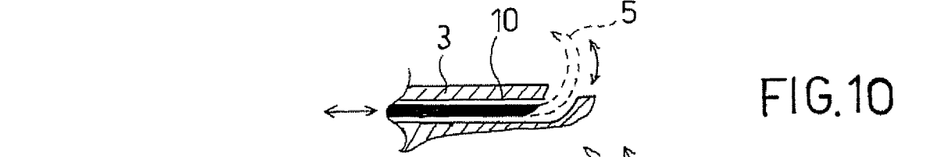
Figure 11:
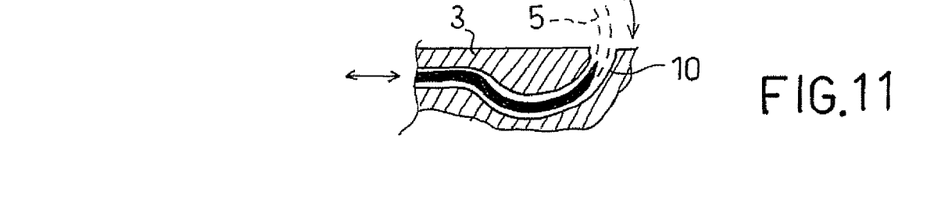

The lateral incision member 5 comprises preferably a hook-shaped RF emitting wire which is slidably housed in a guide seat 10 having an exit opening in the external surface of one of the two opposite large sides 31, 32 of the insertion shaft 3. Preferably, the exit opening of the guide seat 10 is arranged on a lower side 32 of the insertion shaft 3 facing in the direction of lateral offset of the grip portion 6 with respect to the insertion shaft 3 in a manner that, in its operational position the lateral incision member 5 protrudes laterally in the offset direction of the grip portion 6. The guide seat 10 can be curved (FIG. 11) in order to adapt to the shape of the curved RF wire or, alternatively, the guide seat 10 is straight (FIG. 10) and the RF wire is made of an elastically deformable material such that upon retraction into the guide seat 10, the wire straightens and adapt to the shape of the seat and after exiting the straight guide seat 10, the wire returns elastically in its original hooked shape. As already mentioned before, in its operational position the lateral incision member 5 assumes or has a hook shaped configuration protruding from the lower large side 32 of the insertion shaft 3 laterally in the direction of offset of the grip portion 6 with respect to the insertion shaft 3 and a free end 33 of the hook shaped wire is pointing proximally substantially towards the handle portion 2. This particular configuration enables to perform a very precise lateral cut during proximal withdrawal of the instrument 1 from the operation site, as will be described later.

Figure 5:
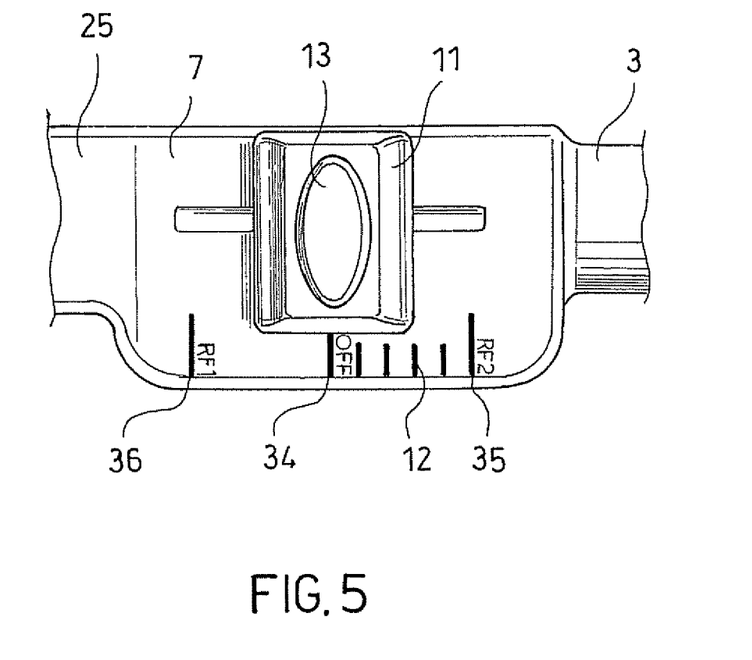
FIG. 5 is en enlarged view of a further detail of the instrument according to an embodiment of the invention.

The movement of the lateral incision member 5 from the rest position in the operational position and vice versa is caused by a moving mechanism arranged inside the handle portion 2 and connected to the lateral incision member 5 by means of a movement transmitting means, e.g. a push rod and/or a pulling wire (not shown) housed inside the insertion shaft 3. The moving mechanism is manually operable by an adjustment knob or cursor 11 arranged at the operating portion 7 of the handle 2. The adjustment cursor 11 is preferably arranged on an upper large side 31 of the operating portion 7 opposite the lower large side 32 from which the lateral incision member 5 protrudes. In other words, the adjusting cursor faces in the direction of lateral offset of the insertion shaft 3 with respect to the distal grip portion 6 of the handle 2. As shown in the close-up view of FIG. 5, the adjustment cursor 11 can be translated in the (distal-proximal) longitudinal direction of the instrument 1 and selectively positioned in one of the following positions:
- a neutral OFF position 34, in which the lateral incision member 5 is completely retracted in its rest position within the overall encumbrance of the insertion shaft 3 and both the distal incision tip 4 and the lateral incision member 3 are de-energized and cannot be energized;
- a plurality of different distal RF2 positions 35 which correspond to different operative positions of the lateral incision member 5 selectable by the surgeon in order to adjust the extent of lateral protrusion of the lateral incision member 5. When the adjusting cursor 11 is brought to one of these RF2 positions, the extent of the cursor movement is transmitted by the movement transmitting means to the lateral incision member 5, which will be laterally extracted accordingly. When the adjusting cursor 11 is in the RF2 position 35, it is possible to energize the lateral incision member 5 with RF current for the lateral dissection of tissue, while the distal incision tip 4 remains de-energized;
- a proximal RF1 position 36, in which the lateral incision member 5 is completely retracted in its rest position within the overall encumbrance of the insertion shaft 3 and only the distal incision tip 4 can be energized, while the lateral incision member 5 remains de-energized.

Advantageously, visible and/or tactile markings 12 indicating the OFF, RF1 and the different RF2 positions of the adjusting cursor 11 are provided along its track in order to allow for permanent visualization or tactile control of the depth of the lateral cut and the general state of the instrument 1. In the embodiment depicted in the figures, the markings 12 define a millimeter scale for adjusting the extent of protrusion of the lateral incision member 5 in its operational position. Of course a different, e.g. imperial unit, scale is possible, too. The supply of RF current is controllable by a RF activation button 13 which co-operates with switches in the RF conductor means that connect the external RF connector 9 with the distal incision tip 4 and with the lateral incision member 5.

In accordance with a preferred embodiment, the RF activation button 13 is housed or integrated in the adjusting cursor 11 (as shown in FIG. 1) and configured in a manner that:
- when the adjusting cursor 11 is placed in its OFF position 34, pressure activation of the button 13 will not cause any current supply (the button 13 is advantageously mechanically blocked when the cursor 11 is in the OFF position) and both, the distal incision tip 4 and the lateral incision member 5 remain electrically disconnected from the RF connector 9;
- when the adjusting cursor 11 is placed in its proximal RF1 position 36, pressure activation of the RF activation button 13 will close an associated switch, thereby connecting the RF connector 9 electrically with the distal incision tip 4 which is then energized and transmits RF current to the tissue distally adjacent to the insertion shaft end 28. In this position of the adjusting cursor 11, the RF current supply to the lateral incision member 5 is preferably interrupted and prevented.
- when the adjusting cursor 11 is placed on one of the RF2 positions 35, pressure activation of the RF activation button 13 closes an associated switch, thereby connecting the RF connector 9 electrically with the (protracted) lateral incision member 5 which is then energized and transmits RF current to the tissue laterally adjacent to the insertion shaft 3. In this position of the adjusting cursor 11, the RF current supply to the distal incision tip 4 is preferably interrupted and prevented.

Thanks to the integration of the RF activation button 13 in the adjusting cursor 11 which controls the position of the lateral incision member 5, it is possible for the surgeon to operate the instrument 1 with one hand only and to use the second hand for instance for additionally palpate the penetration depth of the instrument through the anus.

The mechanical moving mechanism of the lateral incision member 5 and the RF current conductors and switches will not be described in detail, as they are per se conventional. If a rotational adjusting knob is used instead of the slidable adjusting cursor 11, the moving mechanism of the lateral incision member 5 comprises advantageously a mechanism which converts the rotational movement of the adjusting knob in a translational movement o swiveling movement of the lateral incision member 5. In this case the markings 12 are advantageously arranged angularly spaced around the rotating knob so that the surgeon can immediately read the state of the instrument and or the exact operative position of the lateral incision member 5 corresponding to a given rotational position of the rotating knob.

Figure 3:
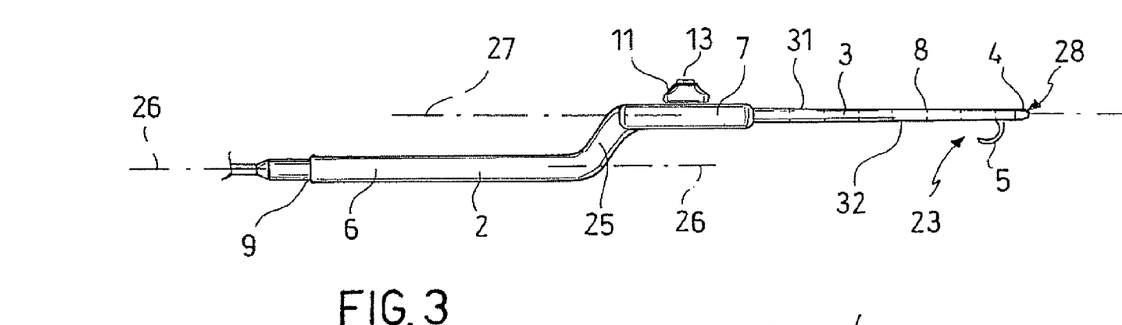
FIG. 3 is a side view of the surgical instrument of FIG. 1.
Figure 4:
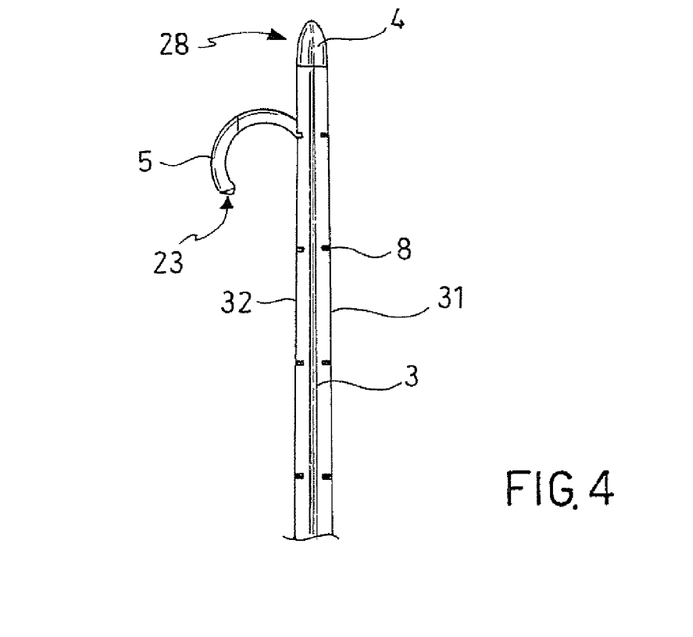
FIG. 4 is an enlarged view of a detail in FIG. 3.

FIGS. 2 and 3 are side views of the instrument 1 in a configuration in which the lateral incision member 5 is completely laterally advanced in its operational position. In this configuration the concave side of the hook shaped RF emitting wire as well as its free end 33 are pointing proximally towards the handle portion 2.

Figure 6:
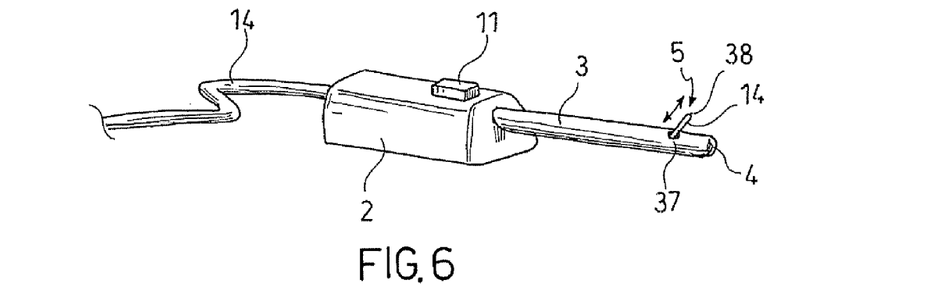
FIG. 6 is an isometric view of a surgical instrument according to a second embodiment of the invention.
Figure 7:
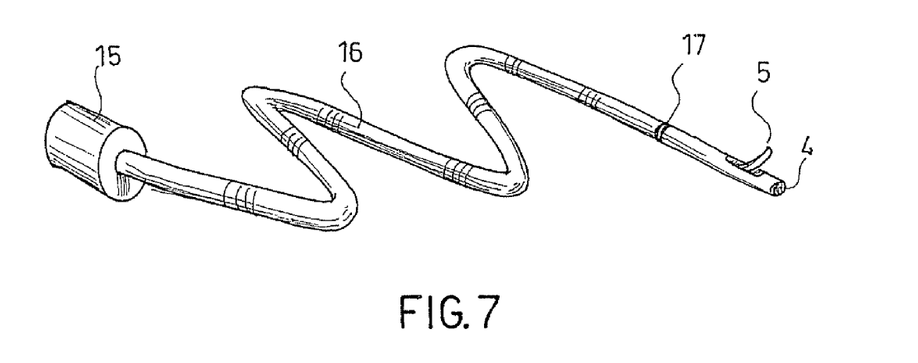
FIG. 7 is an isometric view of a surgical instrument according to a third embodiment of the invention.
Figure 8:
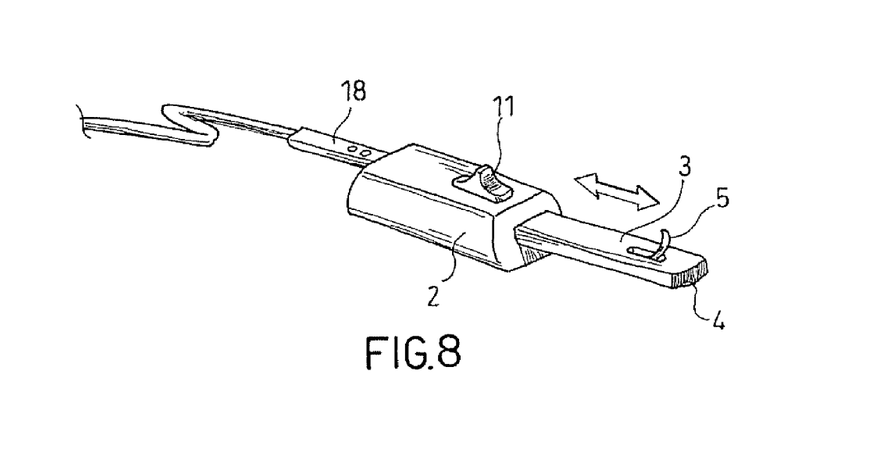
FIG. 8 is an isometric view of a surgical instrument according to a fourth embodiment of the invention.

FIGS. 6, 7 and 8 illustrate alternative embodiments of the invention, wherein like numerals denote like components.

According to the embodiment shown in FIG. 6, the instrument 1 comprises a handle portion 2 and a straight, substantially cylindrical insertion shaft 3. The handle 2 is provided with a slidable adjusting cursor 11 for moving the lateral incision member 5 from the rest position inside the insertion shaft 3 to the operational position, in which the lateral incision member 5 protrudes laterally from the insertion shaft 3. In this embodiment, the lateral incision member 5 comprises a substantially straight RF emitting electrode which, in the operational position, extends from the insertion shaft 3 in a lateral distal direction and is arranged on the same upper side 31 of the instrument as the adjusting cursor 11. The supply of RF current to the distal incision tip 4 and the lateral incision member 5 can be directly controlled by manual controls provided at an external RF current generator (not shown) which is connected to the instrument 1 by a RF conductor wire 14. According to a further aspect of the invention, the RF conductor wire 14 can extend inside the instrument until an exit opening 37 for the lateral incision member 5 and the free end 38 of the conductor wire 14 could per se constitute the lateral incision member 5. In this case, the moving mechanism, i.e. the slidable cursor 11 is directly acting on the RF conductor wire 14 to move it relative to the insertion shaft 3 in order to retract and advance the free end 38 laterally. The further features described with reference to the first embodiment (FIGS. 1-5), particularly the control markings 8, 12 can be analogously applied in the embodiment of FIG. 6.

FIG. 7 shows a further embodiment of the invention, in which the insertion shaft 3 of the instrument 1 is connected to an external RF generator 15 by a flexible cable 16 housing a RF conductor wire (not shown). The flexible cable 16 is preferably detachably snap connected with a proximal connector portion 17 of the rigid insertion shaft 3, thereby electrically connecting the external RF conductor wire with internal conductor wires leading to the distal incision tip 4 and to the lateral incision member 5. The moving mechanism which moves the lateral incision member 5 from its rest position to its operational position and vice versa is connected to flexible transmission means housed inside the flexible cable 16, e.g. flexible push rods or pull wires, which are connected to a moving mechanism arranged at the external RF current generator 15. In this embodiment, the insertion shaft 3 can be completely inserted in the body, e.g. endoscopically, and the movement of the lateral incision member 5 and the RF current supply to both the distal incision tip 4 and the lateral incision member 5 is controlled by means of manual controls arranged at the external RF generator which is placed outside the body of the patient and which is connected to the insertion portion 3 through the flexible cable 16.

Figure 9:
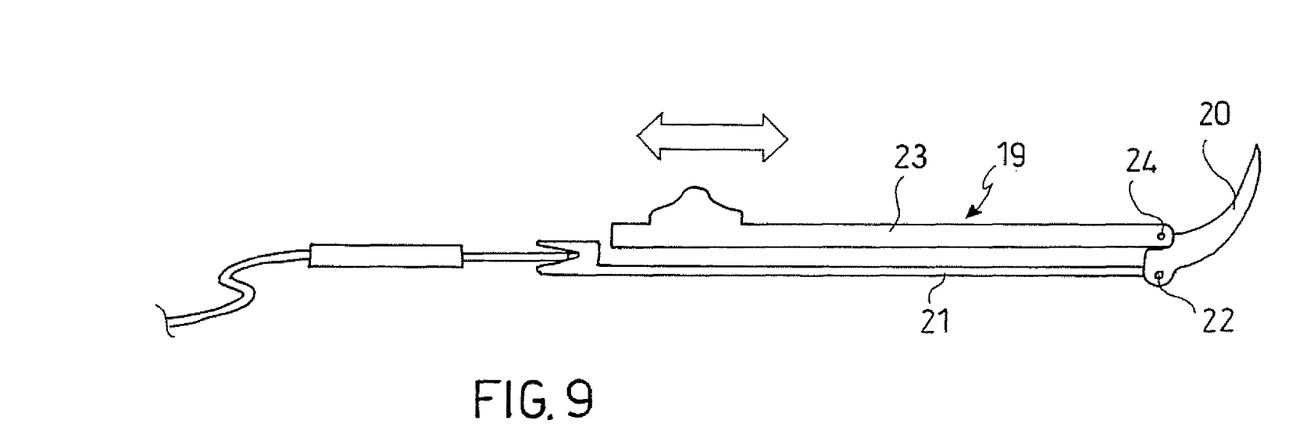
FIGS. 9, 10 and 11 are schematic illustrations of a moving mechanism for moving a lateral incision member of the surgical instrument according to different alternative embodiments of the invention.

FIGS. 8 and 9 illustrate a further embodiment of the invention, in which the RF connector 9 is configured in a manner to receive and electrically contact a surgical RF pen 18 equipped with an own RF current generator (not shown). In this embodiment, the RF current supply to the lateral incision member 5 is directly controlled by the controls of the RF pen 18.

FIG. 9 illustrates an alternative moving mechanism 19 for the movement of the lateral incision member 5 from the rest position to the operational position and vice versa. According to this embodiment, the lateral incision member 5 comprises a curved blade 20 connected to a RF current conductor wire 21 which connects the curved blade 20 electrically with the RF connector portion 17 and hence with the external RF pen 18. The curved blade 20 is rotatably fixed to the insertion shaft 3 such as to swivel about a fixed pivot 22 from a retracted rest position to a laterally protruded operational position. The slidable adjusting cursor 11 is connected to the curved blade 20 by means of a rigid push-pull rod 23 whose distal end is rotatably connected with the curved blade 20 in a second pivot point 24 spaced from the fixed pivot point 22 in a direction transverse to the direction of translation of the adjusting cursor 11 in a manner that a proximal translation of the cursor 11 will cause the curved blade 20 to swivel from the rest position in the operational position and a distal translation of the cursor 11 will cause the curved blade 20 to swivel back into the rest position.

Figure 12:
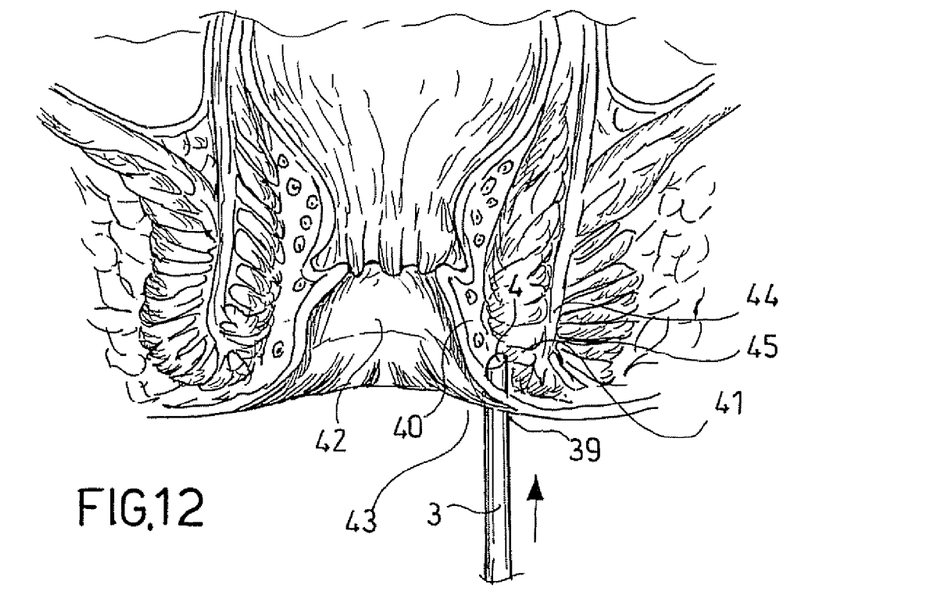
FIGS. 12 and 13 illustrate a method for performing an internal anal sphincterotomy according to an embodiment of the invention using a surgical instrument according to the invention.
Figure 13:
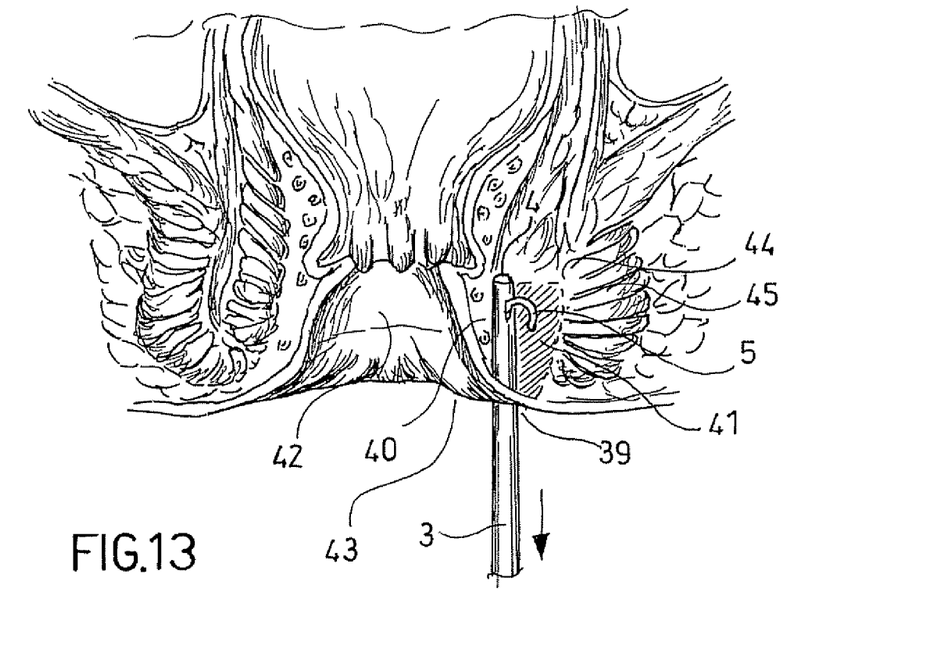

FIGS. 12 and 13 illustrate the use of the surgical instrument 1 according to the invention for performing an internal anal sphincterotomy.

The instrument 1 is connected to a RF current generator and the adjusting cursor 11 is placed in the OFF position. A small perianal skin incision 39 is performed and the distal tip 28 of the insertion shaft 3 is introduced through the skin incision between the anal mucosa 40 and the internal sphincter muscle 41. During insertion, the instrument 1 is oriented in a way that the exit opening for the lateral incision member 5 is facing laterally outward, i.e. away from the anal canal 42 and toward the internal anal sphincter 41. By moving the adjusting cursor 11 from the OFF position 34 to the RF1 position 36 and by pressing the RF activation button 13, the distal incision tip 4 is RF energized thereby dissecting the tissue placed distally ahead of the insertion shaft 3. The insertion shaft 3 is now distally advanced along the internal side of the internal sphincter muscle 41 to the desired location. The markings 8 on the insertion shaft 3 provide an immediate visual control of the depth of distal penetration of the insertion shaft 3. Additionally but not necessarily the surgeon can control the depth of penetration by manually palpating the distal tip of the insertion shaft through from the anal canal 42 through the anal mucosa 40. Once the insertion shaft 3 of the instrument has been advanced to the desired location, the distal incision tip 4 can be de-energized in order not to damage the surrounding tissue. This can be done by releasing the RF activating button 13 and subsequent shifting of the adjusting cursor 11 from the RF1 position 36 to the OFF position 34. Further distal shifting of the adjusting cursor 11 to a RF2 position 35 will cause the moving mechanism to laterally extract the lateral incision member 5 from its rest position into an operational position. Thanks to the adjustable moving mechanism, the cursor 11 can be brought to a plurality of different RF2 positions, in which it is held e.g. by snap engagement or by frictional engagement and the lateral incision member 5 can be gradually extracted, e.g. from 1 mm up to maximum 7 mm and can be locked in a desired intermediate or end position by snap engagement, friction or by means of a dedicated locking mechanism. The markings 12 provide continuous visual control of the lateral extracting depth of the lateral incision member 5. By pressing the RF activating button 13 the lateral incision member 5 is energized with RF current such that it can dissect tissue lateral to the insertion shaft 3. With the lateral incision member 5 energized, the insertion shaft 3 is gently proximally retracted towards the anal verge 43, the lateral incision member 5 thereby dissecting the internal sphincter muscle 41. In this manner a controlled sphincterotomy in both the longitudinal depth and the lateral depth can be performed.

Performing the sphincterotomy in this particular way, i.e. by introducing the instrument between the anal mucosa and the internal sphincter, the lateral incision member 4 is advantageously facing away from the anal mucosa and effectively separated therefrom by the insertion shaft 3. This feature advantageously excludes the risk of trauma of the anal mucosa during the sphincterotomy, thereby preventing the occurrence of post operative fistula. As will be immediately appreciated by the skilled person, the instrument according to the invention obviates the need to rotate a cutting instrument inside the wound before performing the lateral cut through the internal sphincter and allows for a continuous visual control of the insertion depth of the distal tip of the instrument and of the extent of lateral protrusion of the lateral incision member. As a result, the surgeon can easily control the extent of longitudinal and lateral dissection of the internal sphincter and adapt it to the individual anatomic conditions of the patient. Moreover, the incision is smaller than the incisions performed by prior art devices. Thanks to the radio frequency emitting incision devices, the tissue is dissected and the blood is coagulated, thereby reducing the amount of blood spillage. The surgical instrument according to the invention consents to standardize the procedure of myotomies, particularly that of internal anal sphincerotomies and thanks to the greater precision of the dissecting of the internal sphincter, post operative complications such as incontinence, ineffectiveness of the operation and fissure recurrence is reduced compared to conventional techniques and instruments.

According to an alternative method for performing the anal shincterotomy, the instrument 1 is connected to a RF current generator and the adjusting cursor 11 is placed in the OFF position. A small perianal skin incision is performed and the distal tip of the insertion shaft 3 is introduced through the skin incision in the intersphincteric plane between the internal anal sphincter and the external anal sphincter muscle. During insertion, the instrument is oriented in a way that the exit opening for the lateral incision member 4 is facing medially, i.e. towards the anal canal and toward the adjacent internal anal sphincter which needs to be dissected. By moving the adjusting cursor 11 from the OFF position to the RF1 position and by pressing the RF activation button 13, the distal incision tip 4 is RF energized allowing dissection of the tissue placed distally ahead of the insertion shaft 3. The insertion shaft 3 is now distally advanced in the intersphincteric plane to the desired location. The markings 8 on the insertion shaft 3 provide immediate visual feedback of the depth of distal penetration of the insertion shaft 3. Additionally but not necessarily the surgeon can control the depth of penetration by manually palpating the distal tip of the insertion shaft from the anal canal through the anal mucosa.

Once the insertion shaft of the instrument has been advanced to the desired location, the distal incision tip 4 can be de-energized in order not to damage the surrounding tissue. This can be done by releasing the RF activating button 13 and subsequent shifting of the adjusting cursor 11 from the RF1 position to the OFF position. Further distal shifting of the adjusting cursor 11 to a RF2 position will cause the moving mechanism to laterally extract the lateral incision member 5 from its rest position into an operational position. Thanks to the adjustable moving mechanism, the cursor 11 can be brought to a plurality of different RF2 positions, in which it is held e.g. by snap engagement or by frictional engagement and the lateral incision member 5 can be gradually extracted, e.g. from 1 mm up to maximum 7 mm and can be locked in a desired intermediate or end position by snap engagement, friction or by means of a dedicated locking mechanism. The markings 12 provide continuous visual feedback of the lateral extracting depth of the lateral incision member 5. By pressing the RF activating button 13 the lateral incision member 5 is energized with RF current such that it can dissect tissue lateral to the insertion shaft 3. With the lateral incision member 5 energized, the insertion shaft 3 is gently proximally retracted towards the anal verge, the lateral incision member 5 thereby dissecting the internal sphincter muscle. In this manner a controlled sphincterotomy in both the longitudinal depth and the lateral depth can be performed. The advantages of this alternative method for performing a controlled internal anal sphincterotomy are similar to those described in relation with the method illustrated in FIGS. 12 and 13.

Although preferred embodiments of the invention have been described in detail, it is not the intention of the applicant to limit the scope of the claims to such particular embodiments, but to cover all modifications and alternative constructions falling within the scope of the invention.

For instance, even though in the preferred embodiment, the distal grip portion 6 is substantially parallel and transversally offset with respect to the insertion shaft 3 thereby defining a step 25 between the grip portion 6 and the insertion shaft 3, according to an alternative embodiment, the distal grip portion 6 can be substantially aligned with respect to the insertion shaft 3.

According to a yet further development of the invention, the grip portion or handle portion of the instrument and the insertion shaft are connected via an elongate flexible shaft portion enabling endoscopic introduction of the insertion shaft, for instance for performing an endoluminal mucosa resection (EMR) and or other resections or incisions similar to or different from EMR.

The invention claimed is:

1. A surgical instrument (1) for performing controlled myotomies, particularly for performing internal anal sphincterotomies, comprising
a proximal handle portion (2),
an elongate insertion shaft (3) connected with the handle portion (2) and extending distally therefrom,
a distal incision tip (4) arranged at a distal end of the insertion shaft (3) and adapted to incise tissue distally adjacent to the insertion shaft (3),
a lateral incision member (5) arranged at the insertion shaft (3) and adapted to incise tissue laterally adjacent to the insertion shaft (3),
wherein the lateral incision member (5) is movable from a rest position, in which it is retracted towards or inside the insertion shaft (3) and an operational position in which it protrudes laterally from the insertion shaft (3),
wherein the insertion shaft (3) is substantially rigid and straight and has an elongate flattened shape defining a reference plane, wherein the lateral incision member (5) can be protracted transversely to the reference plane of the insertion shaft (3).

2. A surgical instrument (1) according to claim 1, wherein the insertion shaft (3) comprises markings (8) for a visual or tactile control of the insertion depth of the insertion shaft (3), said markings defining a graduated scale.

3. A surgical instrument (1) according to claim 1 or 2, comprising an adjusting knob or cursor (11) connected with the lateral incision member (5) by a moving mechanism, wherein said adjusting cursor (11) can be placed along an adjusting track in a number of different positions (RF2) in order to adjust the operational position of the lateral incision member (4).

4. A surgical instrument (1) according to claim 3, comprising visible or tactile markings (12) arranged along the adjusting track of the adjusting knob or cursor (11) for providing a continuous visible or tactile control of the lateral protrusion of the lateral incision member (5).

5. A surgical instrument (1) according to claim 1, wherein at least one of the distal incision tip (4) and the lateral incision member (5) comprise an electrode tip suitable to transmit radiofrequency current to the tissue for dissecting the tissue and coagulating the blood.

6. A surgical instrument (1) according to claim 5, wherein the distal incision tip (4) comprises a blunt radiofrequency current electrode and the lateral incision member (5) comprises a hook-shaped radiofrequency current wire.

7. A surgical instrument (1) according to claim 5, comprising an RF activation button (13) which interacts with RF conductor means connecting an external RF connector (9) with the distal incision tip (4) and with the lateral incision member (5) for selectively energizing and de-energizing them.

8. A surgical instrument (1) according to claim 7, comprising an adjusting knob or cursor (11) connected with the lateral incision member (5) by a moving mechanism, wherein said adjusting cursor (11) can be placed in a number of different positions (RF2) in order to adjust the operational position of the lateral incision member (5), wherein said RF activation button (13) is housed in said adjusting cursor (11).

9. A surgical instrument (1) according to claim 1, wherein the lateral incision member (5) is positioned near the distal end of the insertion shaft (3).

10. A surgical instrument (1) according to claim 1, wherein the handle portion (2) comprises a distal grip portion (6) substantially parallel and transversally offset with respect to the insertion shaft (3) thereby defining a step (25) between the grip portion (6) and the insertion shaft (3).

11. A surgical instrument (1) according to claim 1, wherein the handle portion (2) is connected to the insertion shaft (3) via an elongate flexible shaft portion adapted to enable endoscopic introduction of the insertion shaft (3).

12. A surgical method for performing a myotomy comprising the following steps:
providing a surgical instrument (1) comprising:
a proximal handle portion (2),
an elongate insertion shaft (3) connected with the handle portion (2) and extending distally therefrom,
a distal incision tip (4) arranged at a distal end of the insertion shaft (3) and adapted to incise tissue distally adjacent to the insertion shaft (3),
a lateral incision member (5) arranged at the insertion shaft (3) and adapted to incise tissue laterally adjacent to the insertion shaft (3),
wherein the lateral incision member (5) is movable from a rest position, in which it is retracted towards or inside the insertion shaft (3) and an operational position in which it protrudes laterally from the insertion shaft (3),
wherein the insertion shaft (3) is substantially rigid and straight and has an elongate flattened shape defining a reference plane, wherein the lateral incision member (5) can be protracted transversely to the reference plane of the insertion shaft (3);
inserting the instrument with its insertion shaft towards a target location by dissecting tissue distally adjacent to the insertion shaft with a distal incision tip of said instrument, while a lateral incision member is retracted in a rest position towards or inside the insertion shaft;
extracting the lateral incision member in an operational position laterally from the insertion shaft;
dissecting tissue laterally adjacent to the insertion shaft by withdrawing the insertion shaft proximally or advancing the insertion shaft distally with the lateral incision member protruding in its operational position.

13. A surgical method according to claim 12, comprising the steps of performing an internal anal sphincterotomy, introducing the instrument between the anal mucosa and the internal sphincter by dissecting tissue distally adjacent to the insertion shaft with the distal incision tip of the instrument, protracting the lateral incision member laterally into the internal sphincter and dissecting the internal sphincter with the lateral incision member by withdrawing the insertion shaft proximally towards the anal verge with the lateral incision member protracted in its operational position.

* * * * *